US005755755A

United States Patent [19]
Panyard

[11] Patent Number: 5,755,755
[45] Date of Patent: May 26, 1998

[54] THERAPEUTIC STRUCTURE AND METHOD

[76] Inventor: Albert A. Panyard, 53740 Andrew Cir., New Baltimore, Mich. 48047

[21] Appl. No.: 787,025

[22] Filed: Jan. 28, 1997

Related U.S. Application Data

[63] Continuation-in-part of Ser. No. 571,475, Dec. 13, 1995, Pat. No. 5,634,940.

[51] Int. Cl.$^6$ .................................................. A61F 7/00
[52] U.S. Cl. ........................... 607/104; 607/108; 607/114
[58] Field of Search ..................... 607/96, 104, 107–112, 607/114; 165/46; 602/2, 5–8

[56] References Cited

U.S. PATENT DOCUMENTS

| | | | |
|---|---|---|---|
| 5,324,319 | 6/1994 | Mason et al. | 607/104 |
| 5,350,418 | 9/1994 | Janevski et al. | 602/21 |
| 5,393,462 | 2/1995 | Avery | 607/114 X |
| 5,405,312 | 4/1995 | Jacobs | 602/5 |
| 5,415,624 | 5/1995 | Williams | 602/21 |
| 5,456,701 | 10/1995 | Stout | 607/107 X |
| 5,634,940 | 6/1997 | Panyard | 607/108 X |

*Primary Examiner*—John P. Lacyk
*Assistant Examiner*—Ryan Carter

[57] ABSTRACT

Structure for and method of therapeutic treatment of a body portion to relieve swelling and pain and facilitate healing of injuries, wounds and incisions. The structure includes a shield adapted to be placed in intimate surface to surface contact with the body portion, a regulator for passing a fluid through the shield at a regulated temperature and/or flow rate, a control for controlling the flow and temperature of the fluid and a temperature sensor for modifying the temperature and flow of the fluid in response to monitored temperature which may be the temperature of the body portion. The shield is constructed of an inner and outer elastomric member, at least the inner member of which is in the mirror image form of the body portion to be treated, which inner and outer members are sealed together to form a pocket, fluid passing structure, which may be manifolded tubing in the form of the body portion within the pocket, and a gelatinuous substance within the pocket positioned between the fluid passing structure and the inner member. The inner and outer members may be directly molded on castings of the body portion and the tube structure may be adhered to the inner surface of the outer member. An air pocket and an air valve may be formed in the outer member. In use, the shield is positioned over a body portion to be treated in intimate surface to surface contact therewith, and fluid is passed through the tube from the regulator at a flow rate and having a temperature controlled by the controller modified by the monitored temperature to provide cryogenic therapy. Air under pressure may be placed in the air pocket to provide compression therapy.

21 Claims, 6 Drawing Sheets

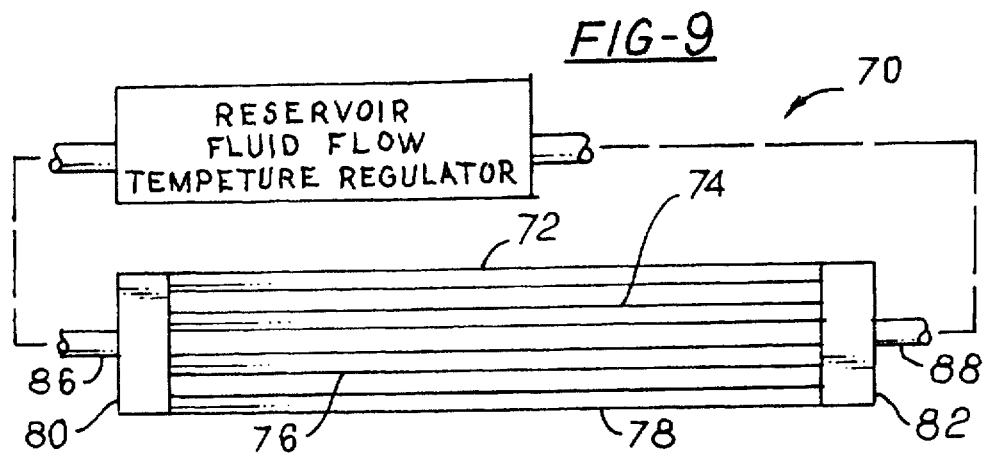
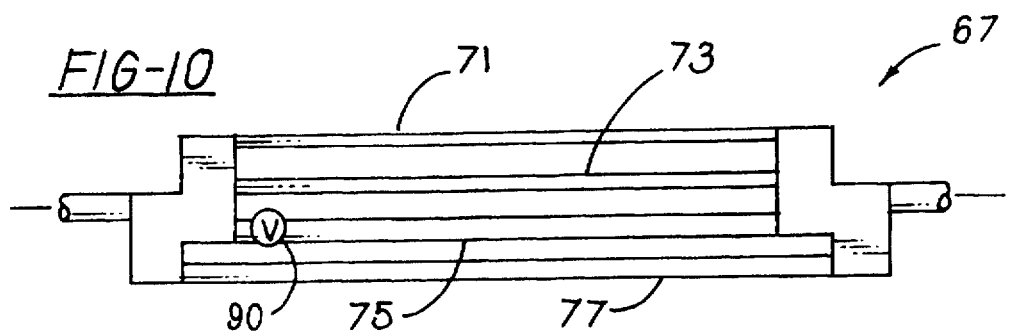
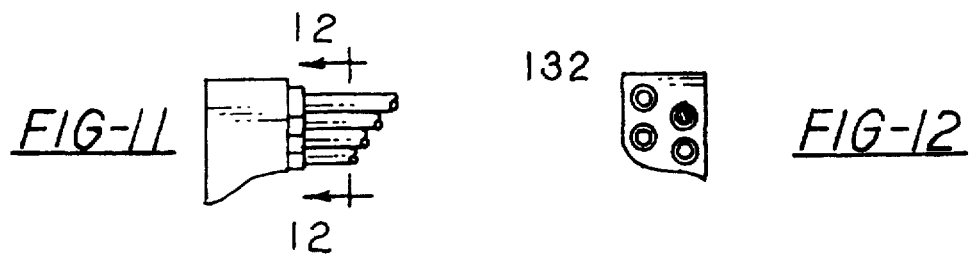
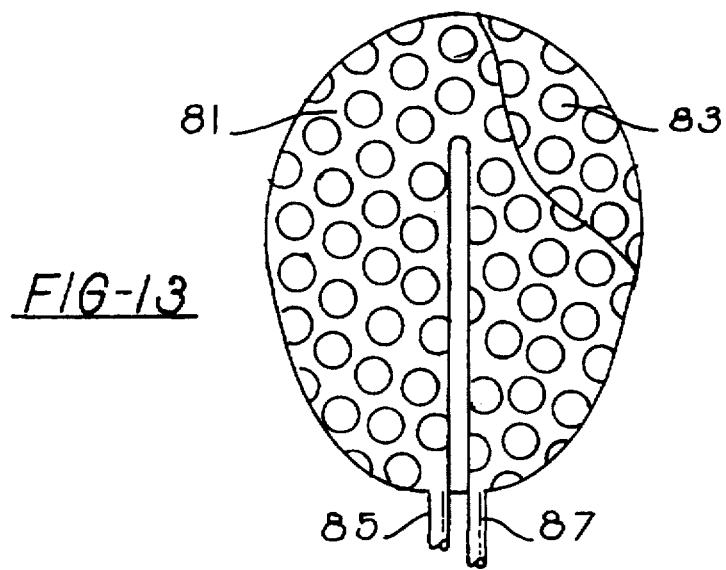

THERAPEUTIC STRUCTURE AND METHOD

CROSS REFERENCE TO RELATED APPLICATION

This application is a continuation in part of patent application, Ser. No. 08/571,475, filed Dec. 13, 1995, now U.S. Pat. No. 5,634,940.

BACKGROUND OF THE INVENTION

1. Field of the Invention

The invention relates to a structure for and method of therapeutic treatment of a body portion requiring maintaining the body portion at a programmed temperature while selectively applying pressure to the body portion and a method of making the structure.

More specifically, the invention refers to a therapeutic device including a selectively inflatable shield having a surface which is the mirror image of a body portion for application to the body portion in intimate surface to surface contact therewith and means for regulating the temperature of the shield by passing a fluid therethrough having a temperature maintained in accordance with a predetermined program and/or the temperature of the body portion.

The invention also specifically refers to the method of therapeutic treatment of the body portion with the device through the application of the shield of the device to the body portion under controlled pressure and in intimate surface to surface contact therewith while regulating the temperature of the shield, and a method of manufacturing the device.

2. Description of the Prior Art

In the past, devices have been known for cooling or heating a body portion such as a knee, ankle, neck or the like to reduce swelling, to promote healing and to relieve pain. Such devices include ice packs, common splints, neck braces, cooled or heated wraps and the like. They also include devices for cooling or heating of a body portion in accordance with the type of injury and/or surgery and/or the time during a healing cycle of the body portion.

Wherein pressure has been applied to a body portion by a prior art device, it has usually been applied by means securing the device to the body portion and has been non-uniform.

The more sophisticated of the prior art devices sometimes are provided with passages therein, through which a liquid from a fluid reservoir is passed to either heat or cool a body portion. With such devices, the fluid has usually been pumped at an inconsistent temperature or has been circulated without pumping, using a thermosiphon principle.

The known devices of the past are inadequate since they are not manufactured to conform intimately to the surface of the body portion to be treated, the temperature of which it is desired to control, whereby they are inefficient. Also, they are uncomfortable in that they are not initially molded to the body portion to conform to the shape of the body portion to be temperature controlled and are bulky. In addition, with prior known devices, temperature control has been non-uniform and inconsistent due to poor surface to surface contact between the shield of the device and the body portion and temperature gradient within the devices. Further, lack of control of the pressure at which the previous devices have been applied to the body portion has prevented efficient practice of compression therapy with the devices.

One such device is found in U.S. Pat. No. 5,411,542. The device as disclosed in this patent is flat and is adapted to be wrapped around ankle and foot body portions. The device has straps for securing it in place and passages for the passing of fluid therethrough. As indicated above, this device is deficient in that it is not constructed to be in close surface to surface contact with a body portion, the temperature of which it is desired to control, and no temperature or pressure control means are shown. In fact, no means for circulating the fluid is shown in this disclosure.

The device shown in U.S. Pat. No. 5,411,541 teaches pumping of fluid through a fluid therapy device and control of the fluid temperature. It does not, however, suggest control of the temperature of the body portion in accordance with the flow of the fluid and/or the temperature of the body portion or control of the pressure at which the device is held against the body portion.

The U.S. Pat. No. 5,372,608 merely teaches a thermosiphon employed for circulating fluid through the therapeutic device shown, and does not suggest any control of the temperature of the fluid other than to have frozen particles such as ice in the fluid container. No pressure control is suggested in this patent.

U.S. Pat. No. 4,745,922 shows a substantially conventional neck brace which is not intended to be in intimate surface to surface contact with the body portion it is intended to immobilize. While U.S. Pat. No. 4,745,922 teaches tubing with heating or cooling fluid passing therethrough, and other articles such as an ice bag placed in the brace next to the body portion to be treated, no adequate temperature or pressure control means is disclosed. Again, the device is strapped to the patient.

None of these prior art devices disclose a shield molded in the shape of a body portion to be treated so as to be in intimate surface to surface contact therewith, or adequate temperature or pressure controls in combination therewith to permit desired cryogenic and compression therapy. Further, these prior art devices do not teach a fluid carrying tube coiled in, or manifolded tubes in, the shape of a body portion having adjacent portions in surface to surface contact with each other or a gel hermetically sealed in a pocket with the coiled tube or tubes for the purpose of maintaining the shield in intimate surface to surface contact with the body portion or an air pocket in the device which is selectively filled with air at a predetermined pressure to provide compression therapy.

SUMMARY OF THE INVENTION

Accordingly, there is a need for therapeutic devices for programmed cooling and/or heating of any portion of the body. The devices should include a part capable of being placed in intimate surface to surface contact with the surface of a body portion under a controlled pressure and should be capable of maintaining the temperature of the body portion in a predetermined program and be responsive to the temperature of the body portion. The device of the present invention includes these features due to its unique construction and methods of manufacture and use and therefore provides desired cryogenic and compression therapy.

In accordance with the present invention, the therapeutic device comprises a shield which includes an inner member manufactured of flexible material to the mirror image of a body portion to be treated and an outer member manufactured to at least the approximate mirror image of the body portion. A coiled tube, manifolded tubes or other structure, shaped to approximate the body portion shape, through which fluid may be passed is secured to the outer member on the inner surface thereof with adjacent portions in surface to surface contact with each other. A gelatinouus substance is positioned between the fluid passing structure and the inner surface of the inner member, which serves to hold the outer surface of the inner member in intimate contact with a body portion to be treated. The shield may also include an inflatable pocket on or in the outer member for controlling the pressure at which the shield is applied to the body portion.

In a preferred method of manufacture of the shield of the therapeutic device of the invention, a cast of the body portion to be treated is made directly from the body portion, an image in the exact shape of the body portion is then made in the cast. Then the inner member of the therapeutic device is produced by molding a layer of flexible elastomer on the image of the body portion to form a mirror image of the body portion.

A subsequent slightly larger than life second image of the body portion is made and the outer member of the shield of the therapeutic device is produced again by molding a relatively thin layer of an elastomer over the larger image of the body portion. An air pocket may be produced in the outer member to aid in compression therapy as will be later considered in more detail.

Both the images of the body portion may be made by first reducing the cast of the body portion to be treated to mathematically exact digital electric signals representative of the surface of the body portion which are stored and later retrieved and used to reproduce an exact body portion image which is life size, larger or smaller than life size in accordance with known technology.

A tube is wound so as to substantially conform to the inner surface of the outer member with the ends of the tube extending out of the outer member for attachment to a fluid reservoir or the like. Alternatively, a plurality of shorter manifolded tubes may be substituted for a single longer tube to reduce the temperature gradient within the device. Also, fluid passages may be produced by selectively heat sealing the members, manufactured in the shape of a body portion to be treated, together.

A gelatinous substance is placed between the inner surface of the inner member and the tube, tubes or other fluid passing structure which are secured to the inner surface of the outer member, and the inner and outer members are sealed together about their periphery. The seal may be a hermetic seal.

An air valve is connected to the outer member to permit selective control of the air pressure in the air pocket in the outer member of the shield.

The complete shield is then connected through the ends of the tube, the manifold or the fluid passing structure to a fluid reservoir including means for heating or cooling the fluid therein and/or regulating the flow of fluid from the reservoir through the fluid passing structure and back to reservoir, and a control is connected to the fluid reservoir which is responsive to structure for sensing the temperature of the body portion to be treated.

In use, the therapeutic device of the invention is placed over a body portion, the temperature of which it is desired to control. Air is passed into the air pocket to place a desired pressure on the body portion and fluid is passed through the fluid passing structure at a controlled temperature and/or controlled fluid flow to maintain the body portion at a programmed variable temperature or a constant temperature, either of which may be responsive to the actual temperature of the body portion to be treated.

In such method of use, the outer surface of the inner member of the shield is held in intimate surface to surface contact with the body portion to be treated due to the flexible nature of the elastomer of which it is made and the omnidirectional forces applied thereto through the gelatinous substance under the pressure applied by air in the air pocket.

Temperature transfer from the fluid in the fluid passing structure, gelatinous substance and inner member of the therapeutic device is enhanced by sections of the fluid passing structure being in contact with each other and with a large portion thereof exposed to the gel and in particular with the gel being in intimate contact with the inner surface of the inner member in a hermetically sealed shield.

Accordingly, with the device of the invention, the temperature of a body portion and pressure applied to the body portion may be controlled as desired without discomfort to the patient. The cryogenic and compression therapy for the body portion may be used to reduce swelling as in sprains or the like during either short or long term treatment of an injury. The device of the invention can be used continuously for hours or days to aid healing and reduce pain without interruption, without discomfort or injury to a patient. Cold fluid may be used during treatment of an injury and as post-operative pain control short or long term therapy or the body part may be warmed to promote healing by passing heated fluid through the temperature controlled therapeutic device.

BRIEF DESCRIPTION OF THE DRAWINGS

FIG. 9. is a partly pictorial, partly diagrammatic view of alternative, manifolded tubing structure for use in the device of FIGS. 14 through 16.

FIG. 10. is a pictorial view of a modification of the manifolded tubing structure shown in FIG. 9.

FIG. 11. is an enlarged partial elevation view of manifolded tubing structure similar to a portion of FIG. 9.

FIG. 12. is a section view of the structure of FIG. 11, taken substantially on the line 12—12 in FIG. 11.

FIG. 13. is an elevation view of another modification of fluid passing structure, constructed in accordance with the invention, for use in a device such as shown in FIGS. 17–20.

DESCRIPTION OF THE PREFERRED EMBODIMENT

Figure 1:
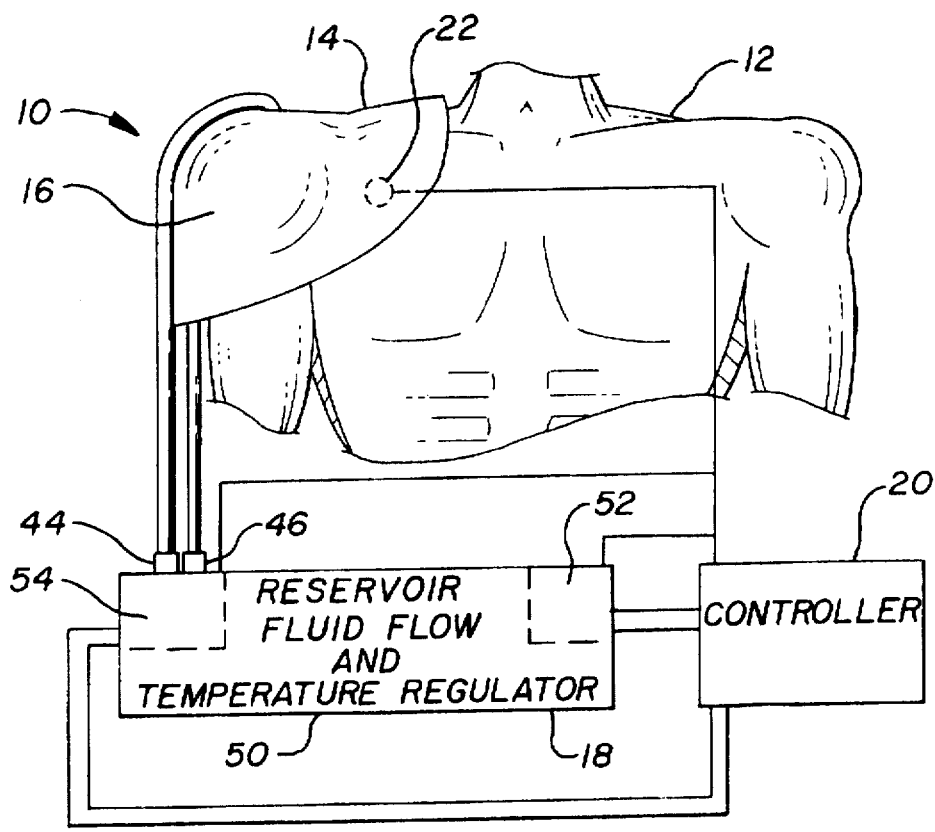
FIG. 1. is a diagrammatic front view of a portion of a patient with the shield of a therapeutic device constructed in accordance with the invention positioned on the right shoulder of the patient, which shield may be constructed and which device is adapted to be utilized in accordance with the methods of the invention.

As shown best in FIG. 1, the therapeutic device 10 of the invention has been formed to treat the right shoulder 16 of a patient 12. The therapeutic device 10 includes a shield 14 constructed in the form of the shoulder 16 of the patient 12. The device 10 further includes a reservoir, fluid flow and temperature regulator structure 18, a controller 20 and a temperature sensor 22.

Figure 2:
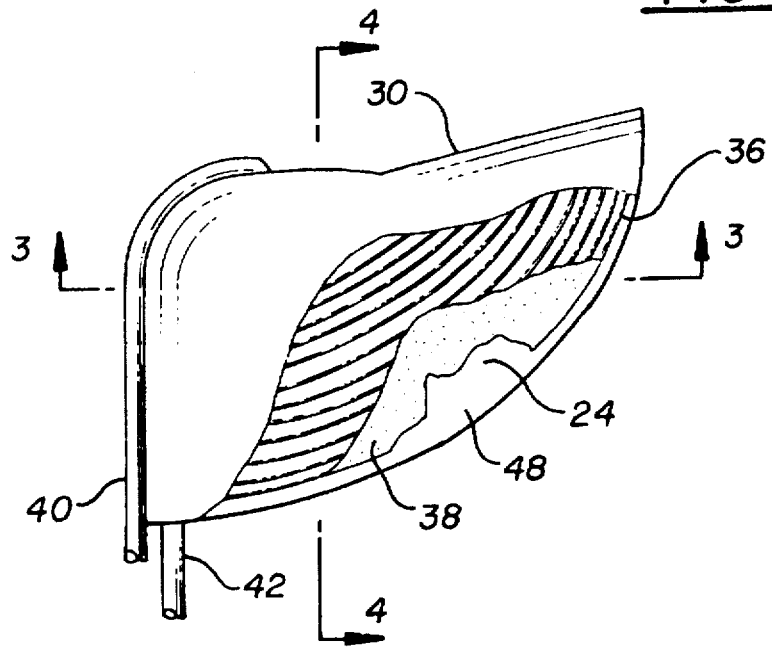
FIG. 2. is an enlarged front view of the shield of the therapeutic device illustrated in FIG. 1, partly broken away to shoe the inner and outer members and the tube and gel of the shield.
Figure 3:
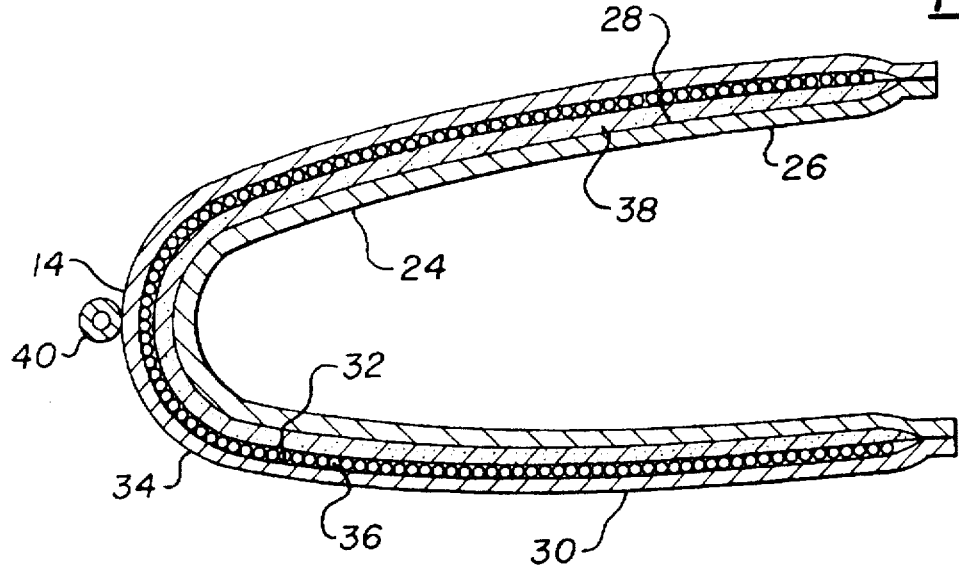
FIG. 3. is an enlarged section view of the shield of the therapeutic device illustrated in FIGS. 1 and 2, taken substantially on the line 3—3 in FIG. 2.
Figure 4:
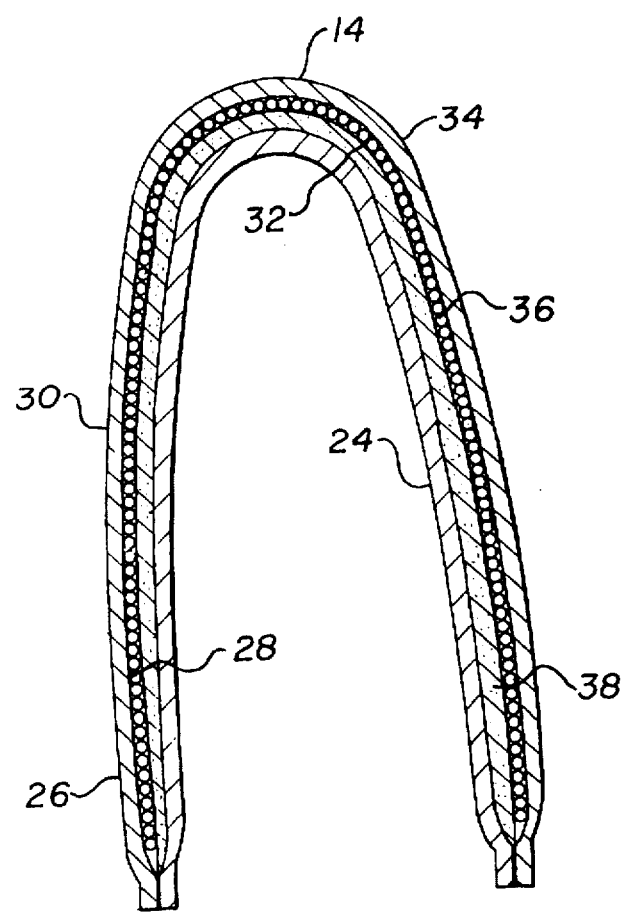
FIG. 4. is another enlarged section view of the shield of the therapeutic device illustrated in FIGS. 1 and 2, taken substantially on the line 4—4 in FIG. 2.
Figure 5:
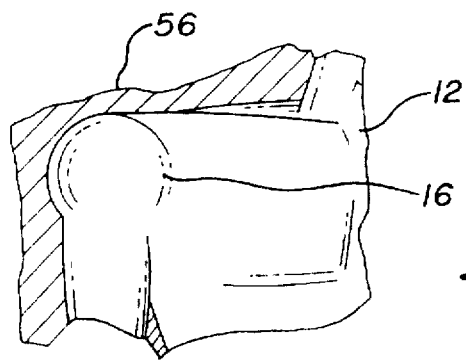
FIG. 5. is an illustration of the first step in producing the shield of the therapeutic device of FIG. 1, illustrating a cast produced on a body portion of a patient.
Figure 6:
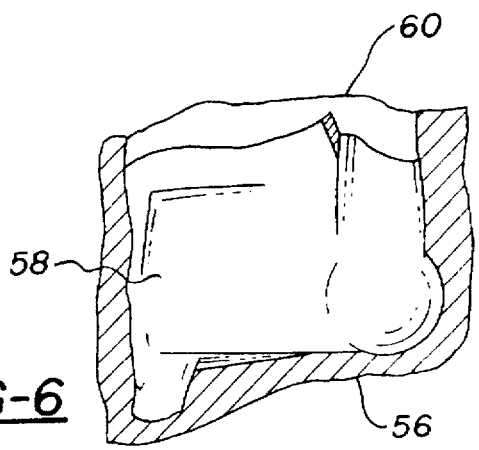
FIG. 6. is an inverted view of the cast shown in FIG. 5, with an exact image of the patient's body portion cast therein.

The shield 14, as shown in more detail in FIGS. 2–4, includes an inner member 24 molded of a thin, flexible elastomer, or like polymer, to the mirror image shape of a patient's body portion, the shoulder 16. The inner member 24 has an outer surface 26 and inner surface 28, as shown best in FIGS. 3 and 4.

The inner member 24 is preferably constructed of an elastomer such as a block copolymer or vulcanizate, which has a memory property. Other materials may be used for the inner member 24, but should have a high degree of flexibility, a memory property and be capable of being molded by any of a number of molding processes to the mirror image of the shape of a human body portion, such as shoulder 16.

An outer member 30 also has an inner surface 32 and an outer surface 34. The outer member 30 is formed in the approximate form of the shoulder 16 of the patient 12, but is slightly larger than the inner member 24 to accommodate coiled tube 36 and a gel, gelatinuous substance or gelatinoid substance 38 in the pocket 48 between the inner and outer members 24 and 30.

Again, the outer member may be constructed of an elastomer and should have a high degree of flexibility and a memory property. Outer member 30 also preferably has an insulating property to slow heat transfer therethrough with the shield 14 in use.

In the shield 14 of the therapeutic device 10, the tube 36 is coiled to form the general shape of the shoulder 16 and is secured as by a suitable adhesive or the like to the inner surface 32 of the outer member 30. The adjacent coiled portions of the tube are in surface to surface contact with each other, as shown best in FIG. 2, to promote fluid temperature transfer therebetween, and thus uniform temperature throughout the shield 14.

The ends 40 and 42 of the tube 36, also constructed of an elastomer, extend out of the shield 14 and are connected to the reservoir, fluid flow and temperature regulator 18 through appropriate connectors 44 and 46.

The gelatinuous substance 38 of the shield 14 is positioned between the tube 36 and the inner shield member 24, and may be a silicon gel. The gelatinuous substance must be soft and pliable at the temperatures of the shield and may be free in the pocket 48 between the inner and outer members 24 and 30, or may be encased in a thin pliable sac within the pocket.

The inner member 24 is heat sealed about its periphery to the periphery of the outer member 30 of the shield 14, with tube 36 and gel 38 being the only material therebetween to complete the shield 14, constructed as shown in FIG. 2. The pocket 48 between the inner member 24 and outer member 30 may, if desired, be vacuum sealed.

Gelatinuous substance 38 serves to maintain the outer surface 26 of the inner member 24 of the shield 14 in intimate surface to surface contact with the shoulder 16 of the patient 12 under the weight of the shield 14 and any fluid passing therethrough and/or pressure applied to the shield 14, due to omnidirectional forces applied to the inner member 24 of the shield 14 through the gelatinuous substance. The gelatinuous substance 38 makes up for any minor body part to shield surface variation by deforming the shield member 14 to conform to the surface of the body part to be treated.

Due to fluid temperature transfer from the tube 36 which is in intinmate contact with the gelatinuous substance 38 and the contact of the gelatinuous substance 38 with the inner member 24 of the shield 14 and the substantial absence of other material such as air in the shield, a high degree of uniform temperature transfer is maintained between a fluid in the tube 36 and the patient's shoulder 16.

The reservoir, fluid flow and temperature regulator 18 includes a reservoir 50 for a liquid such as water, a temperature control 52 and a fluid flow control 54. The temperature control 52 includes means for cooling and/or heating the fluid in the reservoir 50, in accordance with electrical signals from the controller 20. The flow control 54 includes means for controlling the quantity of fluid flowing through the tube 36 per unit time in accordance with electrical signals received from the controller 20.

The controller 20 is an electronic device, preferably digital, which will control the reservoir, fluid flow and temperature regulator 18 to regulate the temperature of the fluid in the reservoir, and thus the temperature of the liquid flowing through the tube 36. The controller 20 further controls the quantity of fluid passing through the tube 36 per unit of time from the regulator, thereby further regulating the temperature of the shield 14 of the therapeutic device 10.

Further, in accordance with the invention, the controller may operate on a predetermined program, that is a program which varies the fluid flow and temperature in a predetermined manner over a predetermined period and the program may be altered at the controller.

In addition, a sensor 22 is provided for sensing the temperature of the body portion, i.e. shoulder 16, and through the controller the sensor 22 is capable of varying the program of the controller to maintain the temperature of the shoulder 16 at a predetermined therapeutic temperature related to the actual temperature of the body portion.

The sensor 22 may sense the temperature of the surface of the shoulder 16 or may sense the shoulder temperature deeper inside the shoulder. Further, the sensor 22 may be connected to supply an electrical signal proportional to the temperature of the shoulder directly to the fluid flow regulator 54 or directly to the temperature regulator 52 instead of to the controller 20 as shown in FIG. 1.

As indicated above, the inner and outer members 24 and 30 of the therapeutic shield 14 are preferably constructed of a flexible elastomer, such as a block copolymer and vulcanizate, which is particularly flexible and has a memory property. The tubing 36, as stated, is for example ¼ inch tubing which may be made out of an elastomer and again is particularly flexible.

The gelatinuous substance is a silicon gel, and transfers cold and heat readily between the tube 36, which also readily transfers cold or heat, and the inner shield member 24 and thus to the shoulder 16 of the patient 12 to which the shield is applied.

Figure 7:
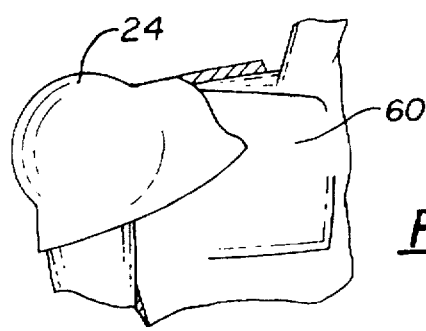
FIG. 7. is a front view showing the inner member of the shield of the therapeutic device of the invention molded on the image of the body portion shown in FIG. 6.
Figure 8:
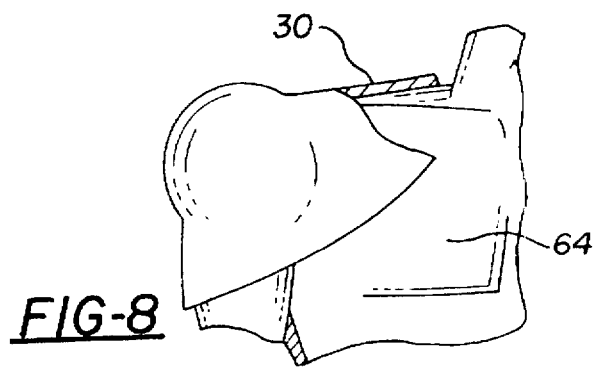
FIG. 8. is a front view of the outer member of the shield of the therapeutic device of the invention molded on a slightly enlarged image of the body portion.

In construction of the shield 14 as shown in FIGS. 5 through 8, a cast 56 is first made of the shoulder 16 of the patient 12. The cast 56 is then removed from the patient and inverted to form the mold 50, shown in FIG. 6, into which is cast a replica 60 of a body portion of the patient 12, that is the shoulder 16. Subsequently, as shown in FIG. 7, a negative image of the form of the shoulder 16 is produced by applying the elastomer of the inner member 24 over the casting 60. A second casting 64 of the shoulder 16, which is slightly larger than the casting 60, is produced and the elastomer for the outer member 30 of the shield 14 is molded on the larger casting 64, a shown in FIG. 8.

Alternatively, the cast 56 may be utilized, after removal from the patient, to mathematically provide electrical signals which are preferably digital, which represent the cast 56 and are stored. Subsequently, the electrical signals are retrieved and used to machine or otherwise produce the castings 60 and 64 on which the inner and outer members 24 and 30 are molded. Mathematical data obtained from the cast 56 would be used to produce high volume manufacturing dies for molding the shield's inner and outer members.

The tube 36 is coiled in surface to surface contact about the inner surface 32 of the outer member 30 with the ends 40 and 42 extending out of the outer member 30 as shown in FIGS. 1 and 2. The coiled tube is adhered to the outer member 30. The gelatinuous substance 38 is positioned between the inner member 24 and the tube 36. The inner member 24 and outer member 30 are then sealed together around their outer periphery to form the shield 14.

The shield 14 is thus particularly adapted to make intimate surface to surface contact with the shoulder 16 or other body portion from which it is modeled and to retain such intimate surface to surface contact with the body portion due to the inclusion of the gelatinuous substance in the pocket 48 formed by the inner and outer members. If considered desirable, on a certain body portion, shield fastening systems may be provided to maintain the shield in position on a patient.

The molded elastomeric shield 14 is thus conformable in that it conforms to the body portion and will maintain a substantially uniform temperature over the entire body portion in intimate surface to surface contact therewith in accordance with the temperature and fluid flow of the fluid flowing through the tube 36.

As alluded to above, in use of the therapeutic device 10 of the invention, the shield 14 constructed as described above, is placed on a body portion, here shoulder 16, that it is desired to maintain at a predetermined or programmed temperature or at a temperature related to the temperature of the body portion, the controller is set to provide the required temperature and fluid flow from the reservoir 50 in accordance with a programmed temperature and fluid flow as modified by the body temperature sensor 22.

With such use of the device 10, a desired therapeutic effect of temperature on an injury or after an operation may be realized with long or short term, close control of the temperature of the body part to be treated. Also, additional damage to a body part injured by a sprain or surgery may be minimized by cooling of the body part with the device 10 before excessive swelling can occur at the sprain. Furthermore, pain can be treated over short or long periods of time by maintaining a body part at a reduced temperature without injury to the body part or discomfort to the patient utilizing the device 10. In addition, pain can be treated for a short period or over an extended period of time by maintaining a body portion at a reduced temperature for selected periods without injury to the body portion or discomfort to the patient.

Also, wherein heat therapy is desired to promote healing, the controller 20 and reservoir, fluid flow and temperature regulator 18 can provide the same type of program as heat therapy to a body portion of a patient as required.

The device 10 as disclosed above is so constructed that the fluid in the shield passes through a single member coiled or otherwise formed in the shield in a single circuitous route. With such structure, the fluid exiting the shield and the fluid entering the shield are at a noticeably different temperature due to the temperature of the body portion on which the shield is placed. Such being the case, the body portion is subjected to differences in temperature which may be substantial and which may be undesirable in the therapeutic treatment of the body portion.

Accordingly, in the substitute fluid passing structure 70 as shown in FIG. 9, in place of a single tube 36 coiled to conform to the body portion with one inlet 40 and one outlet 42, a plurality of short tubes 72, 74, 76 and 78 are connected to an inlet manifold 80 and an outlet manifold 82. Manifold 80 is connected to a source of fluid 84 at a controlled temperature through inlet line 86 while the outlet manifold 82 is connected through a return line 88 to the source of fluid under controlled temperature 84.

With such structure, the tubes 72–78 may all be of the same length and the central portion thereof configured so as to conform to the shape of the body part. The temperature gradient of the tubes 72–78 will be substantially less, since the tubes are shorter than a single tube 36 conformed to the shape of the body portion to be treated as shown in FIGS. 1–4. Thus, the body part will be maintained at a more uniform temperature than with prior devices.

As shown in the modified manifolded structure 67 of FIG. 10, greater control can be asserted over the temperature gradient of the tubes 71, 73, 75 and 77 by, for example, changing the diameter of the different tubes which are in contact with the body portion. As shown in FIG. 10, tubes 71 and 73 are of less diameter and tubes 75 and 77 are of larger diameter. Further, the length of the tubes can be altered as well as the shape of the manifolds to make the temperature gradient between the ends of the tubes more even, particularly in conjunction with tubes of different diameter, again as shown in FIG. 10.

Alternatively, there could be, within the scope of this invention, control valves 90 as shown in FIG. 10 placed in the individual tubes to variably restrict flow therein. Such valves could produce even greater control over the temperature gradient in the tubes. Such valves could be responsive to the temperature of portions of the body portion for which therapeutic treatment is desired in accordance with the concepts disclosed above.

Also as shown in FIGS. 11 and 12, tubes such as tubes 72–78 may be secured lo the manifolds 80 and 82 so that the tubes, at least the major portions of the lengths of the tubes, can be in surface to surface contact with adequate connectors 92 to the manifolds at their ends.

The third embodiment 79 of a fluid passing structure, suitable for use in the shield 116 shown in FIGS. 17–20, includes a first member 81 and a second member 83, either or both of which are preferably manufactured in the shape of the body portion with which they are to be used. The first and second members are then sealed together around their peripheries and at selected places throughout, as shown in FIG. 13, to provide desired fluid flow therethrough. Inlet and outlet tubes 85 and 87 are secured thereto as before.

Figure 14:
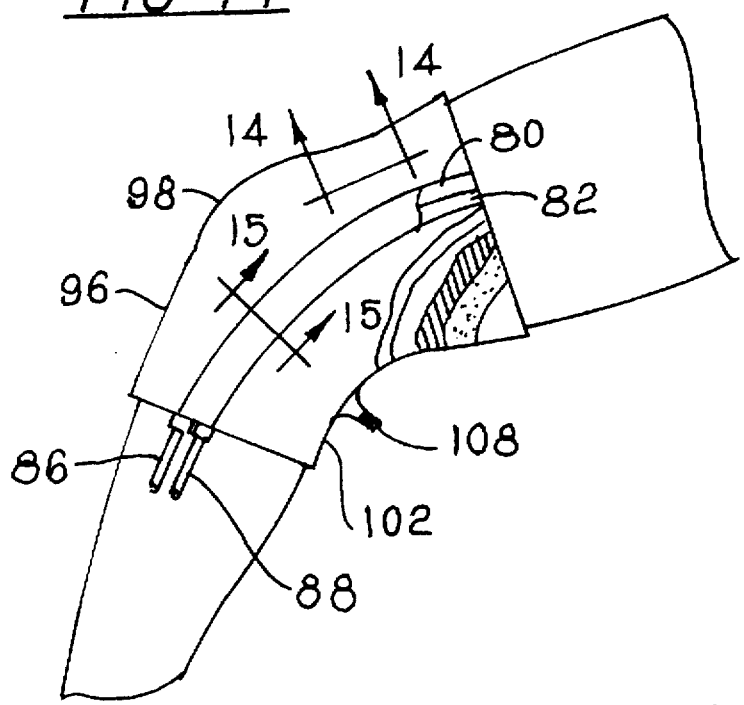
FIG. 14. is a partly broken away elevation view showing a shield of the invention constructed in accordance with the method of the invention for practicing the method of the invention, wherein the body portion is a knee.

The embodiment of the invention shown in FIG. 14 is a therapeutic device 96 manufactured as the device 10 was as explained above to conform to the mirror image of a patient's knee.

The device 96 is a cryogenic and compression therapeutic device. Thus, in use with the controls provided with the device 10 and fluid passage structure as shown in FIGS. 9–12, the device 96 can maintain the temperature of the body portion 98 at a desired temperature for extended periods. Desired pressure may also be applied to the knee area with the device 96 to provide compression therapy as required.

Figure 15:
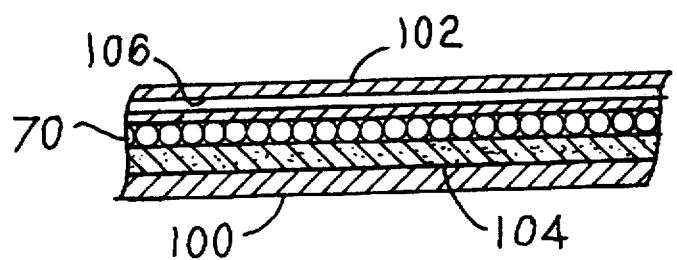
FIGS. 15 and 16, are enlarged, partial section views of the shield of FIG. 14 taken on the lines 15—15 and 16—16 in FIG. 14 respectively.
Figure 16:
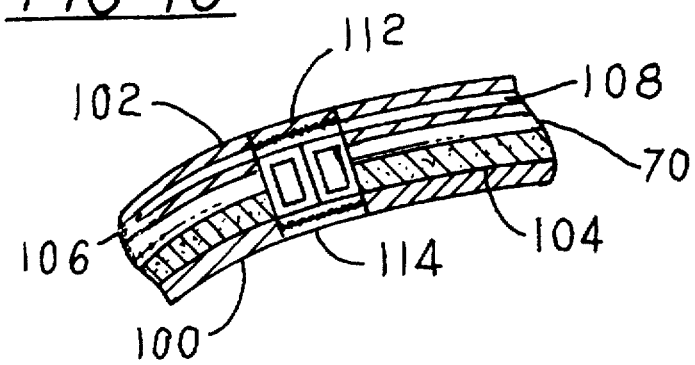
Figure 17:
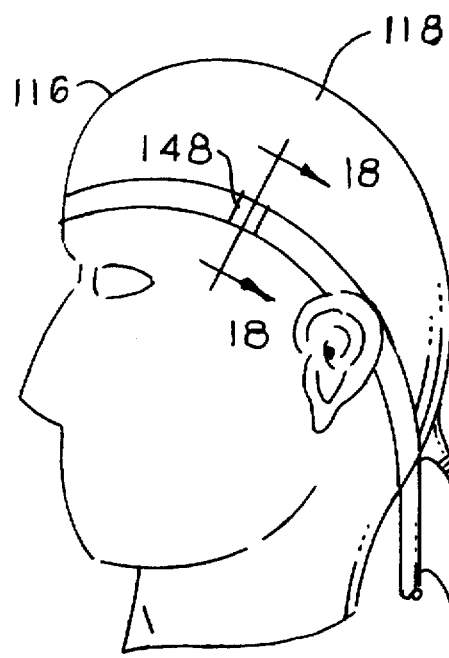
FIGS. 17 and 18 illustrate a partly broken away shield of the invention, constructed in accordance with the method of the invention for practicing the method of the invention, wherein the body portion is the head of a patient.
Figure 18:
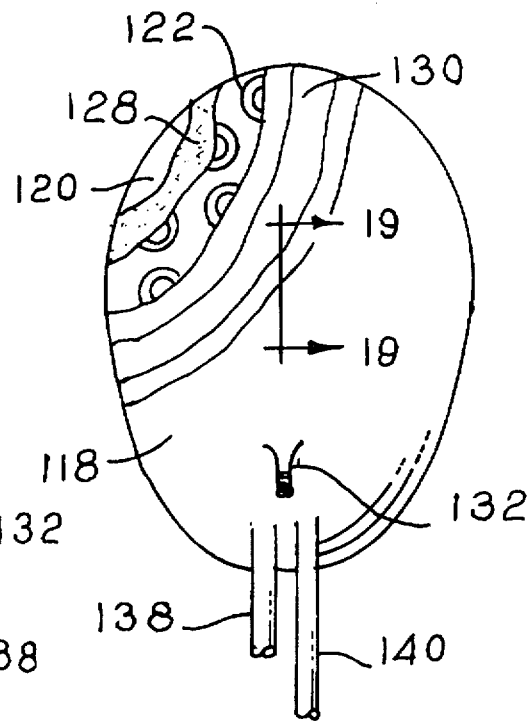
Figure 19:
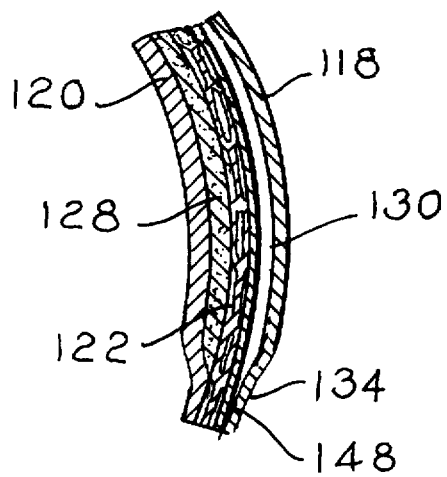
FIG. 19, is an enlarged partial section view of the shield of FIGS. 17 and 18, taken substantially on the line 19—19 in FIG. 17.
Figure 20:
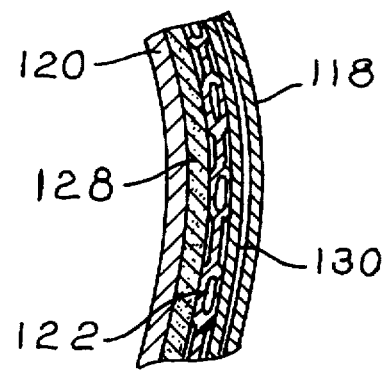
FIG. 20, is an enlarged partial section view of the shield of FIGS. 17 and 18, taken substantially on the line 20—20 in FIG. 18.

As shown in FIGS. 14–16, the device 96 includes the inner member 100, outer member 102, manifolded tube structure 70 including tubes 72–78 and gel 104. This structure is constructed and functions as set forth above.

In addition, the device 96 includes an air pocket 106 in the outer member 102. An air valve 110 is provided in the outer member 106 to permit passage of air under pressure into and out of the air pocket 106. Thus, when the device 96 is in position on a knee 98, pressure may be applied to the knee 98 as required for compression therapy.

The device 96 is held in place on knee 98 by suitable connecting structure secured to manifolds 80 and 82, such as velcro strips 112 and 114 as shown in FIG. 16. The velcro strips also allow minor size adjustment for the device 96 so that the devices may be provided commercially much as clothing is sized, as considered above.

In FIGS. 17–20, the embodiment of the invention is a cryogenic and compression therapeutic device 116 similar to device 96 for use on the head of a patient.

Again, the device 116 includes an outer member 118, an inner member 120, a fluid passing structure 89 connected to tubes 85, gel 128 and air pocket 130.

Headband 134 connects the periphery of the inner and outer members 120 and 118 and the structure 89. Input conduit 85 and an outlet conduit 87 are connected to the structure 89 as shown best in FIG. 20.

An air valve 132 extends through outer member 118.

Buckle 148, or velcro fasteners or the like, may be positioned to connect the parts of the Headband 134, if desired. The connectors again may provide size adjustment for the device 116.

The use of the device 116 is similar to use of the device 96. Again, the device 116 provides cryogenic and/or compression therapy, as needed.

Having thus described the therapeutic structures and methods of the invention in detail, it will be understood that other modifications and embodiments of the invention are contemplated by the inventor.

Thus, the shield may be molded in the form of a foot, an ankle, an elbow, knee, wrist, neck, etc. Also, the cast and molds may be made by any of the molding processes of casting, rotational, injection, co-injection and lost core molding or like molding processes or by other manufacturing methods.

Further, the invention may be used to treat animals and in industry where a manufacturing process requires a programmed temperature and/or compression.

It is therefore the intention to include all embodiments and modifications of the invention disclosed as are defined by the appended claims within the scope of the invention.

I claim:

1. Temperature control structure for a body portion having an outer surface, comprising a shield including an inner member having an outer surface shaped at the time of manufacture to an exact mirror image of the outer surface of the body portion and having a periphery, an outer member having an inner surface and a periphery, means securing the inner and outer members together around their peripheries to form a pocket therebetween, a gelatinous substance in the pocket between the inner and outer members, means at least partly within the pocket between the inner surface of the outer member and the gelatinous substance for regulating the temperature of the shields, means connected to the regulating means for controlling the regulated temperature of the shield and means within the shield operably associated with the gelatinous substance for pressing the gelatinous substance into contact with the inner surface of the inner member.

2. Structure as set forth in claim 1, wherein the means for pressing gelatinous substance into contact with the inner surface of the inner member includes an air pocket in the outer member and means for putting air under selected pressure in the air pocket.

3. Structure as set forth in claim 1, wherein at least the outer surface of the inner member is molded to the mirror image of the outer surface of the body portion.

4. Structure as set forth in claim 1, wherein the means for regulating the temperature of the shield includes at least one tube having a central portion within the pocket and tube ends extending out of the pocket.

5. Structure as set forth in claim 4, wherein the central portion of the tube is coiled within the pocket in the shape of the outer surface of the body portion.

6. Structure as set forth in claim 1, wherein the means for regulating the temperature of the shield is means for circulating the fluid through the pocket.

7. Structure as set forth in claim 6, and further including control means connected to the means for regulating the temperature of the shield for controlling the regulating means in accordance with variable predetermined programs.

8. Structure as set forth in claim 7, and further including sensing means for separately sensing the temperature of the body portion connected to the control means whereby the control means is responsive to the means for sensing the temperature of the body part to control the regulator in accordance with the sensed temperature of the body part.

9. Structure as set forth in claim 1, wherein at least the inner member is constructed of an elastomer which has a memory property which enables the inner member to retain a form which is a mirror image of the body portion, the temperature of which it is desired to control.

10. Structure as set forth in claim 1, wherein the means for regulating the temperature of the shield includes a plurality of tubes having central portions within the pocket and ends connected to separate manifolds connected to a source of a temperature transfer medium outside of the pocket.

11. Structure as set forth in claim 1, wherein the means for regulating the temperature of the shield includes a first and second member, at least one of which is shaped in the mirror image of the body portion and both of which have peripheries, which members are sealed together around their peripheries and at other places within their peripheries to provide passages for fluid circulating between the first and second members.

12. Temperature control structure for a body portion having an outer surface, comprising a shield including an inner member having an outer surface shaped at the time of manufacture to an mirror exact image of the outer surface of the body portion and having a periphery, an outer member having an inner surface and a periphery, means securing the inner and outer members together around their peripheries to form a pocket therebetween, means at least partly within the pocket for regulating the temperature of the shield, and means connected to the regulating means for controlling the regulated temperature of the shield and means for selectively applying a predetermined pressure to the inner member.

13. Temperature control structure for the therapeutic treatment of a body portion having an outer surface comprising a flexible cryogenic shield for treatment of a body portion following trauma of the body portion, which shield has an inner surface shaped at the time manufacture to a form which is an exact mirror image of the outer surface of the body portion, so that the shield is adapted to be placed on the body portion with the inner surface of the shield in intimate surface to surface contact with the outer surface of the body portion and means at least partly within the shield adjacent the inner surface of the shield for regulating the temperature of the shield to program the temperature of the body portion for at least one of reducing pain, slowing swelling and promoting rapid healing of the body portion after trauma of the body portion with the shield placed on the body portion with the inner surface of the shield in intimate surface to surface contact with the outer surface of the body portion.

14. Structure as set forth in claim 13, and further including means connected to the regulating means for controlling the regulated temperature of the shield.

15. Structure as set forth in claim 13, and further including a gelatinous substance with in the shield adjacent to the inner surface of the shield for facilitating intimate surface to surface contact between the shield and body portion under pressure.

16. Structure as set forth in claim 15, and further including means within the shield operably associated with the gelatinous substance for pressing the inner surface of the shield into contact with the outer surface of the body portion under pressure.

17. Structure as set forth in claim 13, wherein the means for regulating the temperature of the shield includes at least one of a tube, manifolds with tubes extending therebetween, and two plastic sheets sealed together about their peripheries and at intermediate points thereover.

18. The method of producing structure for therapeutic treatment of a body portion comprising casting a mold of the negative image of the body portion to be treated, producing an exact mirror image of the body portion from the mold, molding an inner member of flexible material over the image of the body portion having an inner surface which is the negative image of the body portion, producing another image of the body portion which is slightly larger than the image of the body portion, forming an outer member over the larger image of the body portion, hermetically sealing the inner and outer members around the outer periphery thereof to form a pocket therebetween, and providing means for circulating a temperature controlled fluid between the inner and outer members.

19. A method of therapeutic treatment of a body portion comprising providing a cryogenic shield for treatment of a body portion following trauma of the body portion, which shield has an inner surface and an outer surface, manufacturing the inner surface of the shield to an exact mirror image of the body portion, placing the shield on the body portion with the inner surface of the shield in intimate, surface to surface contact with the body portion and regulating the temperature of the shield to program the temperature of the body portion to facilitate at least one of reducing pain, slowing swelling and promoting rapid healing of the body portion.

20. The method as set forth in claim 19, and further including placing a gelatinous substance within the shield adjacent the inner surface of the shield for facilitating the placing of the inner surface of the shield in intimate, surface to surface contact with the outer surface of the body portion under pressure.

21. The method as set forth in claim 19, and further including placing means within the shield to facilitate pressing the inner surface of the shield into intimate, surface to surface contact with the outer surface of the body portion under pressure and pressing the inner surface of the shield into surface to surface contact with the outer surface of the body portion under pressure using said means.

* * * * *